US011617723B2

(12) United States Patent
Kim et al.

(10) Patent No.: US 11,617,723 B2
(45) Date of Patent: Apr. 4, 2023

(54) COMPOSITION FOR HEPATIC ARTERIAL CHEMOEMBOLIZATION USING HUMAN SERUM ALBUMIN NANOPARTICLES CARRYING ANTICANCER AGENT, AND METHOD FOR PRODUCING SAME

(71) Applicants: SOGANG UNIVERSITY RESEARCH FOUNDATION, Seoul (KR); SEOUL NATIONAL UNIVERSITY R&DB FOUNDATION, Seoul (KR); IMGT CO, LTD., Seongnam-si (KR)

(72) Inventors: Hyun Cheol Kim, Seoul (KR); Jin Wook Chung, Seoul (KR); Eun Ah Jung, Seoul (KR)

(73) Assignees: SOGANG UNIVERSITY RESEARCH FOUNDATION, Seoul (KR); SEOUL NATIONAL UNIVERSITY R&DB FOUNDATION, Seoul (KR); IMGT CO, LTD., Seongnam-si (KR)

( * ) Notice: Subject to any disclaimer, the term of this patent is extended or adjusted under 35 U.S.C. 154(b) by 68 days.

(21) Appl. No.: 16/337,319

(22) PCT Filed: Sep. 27, 2017

(86) PCT No.: PCT/KR2017/010744
§ 371 (c)(1),
(2) Date: Mar. 27, 2019

(87) PCT Pub. No.: WO2018/062865
PCT Pub. Date: Apr. 5, 2018

(65) Prior Publication Data
US 2020/0030246 A1 Jan. 30, 2020

(30) Foreign Application Priority Data
Sep. 27, 2016 (KR) .................. 10-2016-0124304
Sep. 27, 2017 (KR) .................. 10-2017-0125169

(51) Int. Cl.
| | |
|---|---|
| A61K 9/51 | (2006.01) |
| A61K 9/16 | (2006.01) |
| A61K 31/337 | (2006.01) |
| A61K 31/396 | (2006.01) |
| A61K 31/7068 | (2006.01) |
| A61K 47/42 | (2017.01) |
| A61K 49/04 | (2006.01) |

(52) U.S. Cl.
CPC .......... *A61K 9/5169* (2013.01); *A61K 9/1658* (2013.01); *A61K 31/337* (2013.01); *A61K 31/396* (2013.01); *A61K 31/7068* (2013.01); *A61K 47/42* (2013.01); *A61K 49/04* (2013.01)

(58) Field of Classification Search
None
See application file for complete search history.

(56) References Cited

U.S. PATENT DOCUMENTS

2013/0252900 A1* 9/2013 Reb ................ A61K 9/1682
514/17.2
2015/0231075 A1 8/2015 Kangas
2017/0080114 A1* 3/2017 Kim ................ A61K 9/0019

FOREIGN PATENT DOCUMENTS

| EP | 2937080 A1 | 10/2015 |
|---|---|---|
| JP | 2015526510 A | 9/2015 |
| KR | 10-2003-0078722 A | 10/2003 |
| KR | 10-2011-0035136 A | 4/2011 |
| KR | 10-2015-0131435 A | 11/2015 |
| WO | 2015141917 A1 | 9/2015 |

OTHER PUBLICATIONS

Ikeda (J Gastroenterol (2010) 45:60-67).*
Das (Indian J Pharmacol. Jul.-Aug. 2011; 43(4): 409-413).*
Lohcharoenkal et al. (Biomed Research International vol. 2014, Article ID 180549).*
Kawakishi (Agric. Biol. Chem., 47 (9), 2071-2076 (1983).*
Aoyama et al. (Cancer Chemother Pharmacol (1992) 31 (Suppl I)LS55-59).*
Park et al., "Chemoembolization of Hepatocellular Carcinoma: Long-term Survival and Prognostic Factors", Journal of the Korean Radiological Society, 1996, vol. 35, No. 3, pp. 315-323.
Fu et al., "Phase I Trial of Hepatic Arterial Infusion of Nanoparticle Albumin-Bound Paclitaxel: Toxicity, Pharmacokinetics, and Activity", Molecular Medicine in Practice, 2011, vol. 10. No. 7, pp. 1300-1307.
Xin et al., "Efficacy of iodinate oil magnetic paciitaxel albumin nanoparticle on rat liver cancels", Chinese Journal of Cancer Biotherapy, 2011, vol. 18, No. 6, pp. 658-662.
Kim et al., "Capillary microfluidics-derived doxorubicin-containing human serum albumin microbeads for transarterial chemoembolization of hepatic cancer", Materials Science and Engineering C, 2016, vol. 62, pp. 391-397.

(Continued)

*Primary Examiner* — Patricia Duffy
*Assistant Examiner* — Garen Gotfredson
(74) *Attorney, Agent, or Firm* — Vorys, Sater, Seymour and Pease LLP; Mih Suhn Koh

(57) ABSTRACT

The present invention aims to dramatically increase the effect of hepatic arterial chemoembolization by developing human serum albumin-based nanoparticles, which are bioproteins that effectively carry Adriamycin in place of Adriamycin, an anticancer agent used in hepatic arterial chemoembolization. The human serum albumin nanoparticles carrying the Adriamycin not only intensively infiltrate the drug effectively into the cells but also have a synergistic effect that can induce a long-term therapeutic effect by utilizing the effect of continuous drug release from the particles.

13 Claims, 12 Drawing Sheets

(56) References Cited

OTHER PUBLICATIONS

International Search Report for Corresponding International Application No. PCT/KR2017/010744 (dated Jan. 31, 2018) (3 Pages).
Jeon et al., "Transcatheter intra-arterial infusion of doxorubicin loaded porous magnetic nano-clusters with iodinated oil for the treatment of liver cancer", Biomaterials, 2016, pp. 25-33, vol. 88.
Dreis et al., "Preparation, characterisation and maintenance of drug efficacy of doxorubicin-loaded human serum albumin (HSA) nanoparticles", International Journal of Pharmaceutics, 2007, pp. 207-214, vol. 341.
Lentacker et al., "Design and Evaluation of Doxorubicin-containing Microbubbles for Ultrasound-triggered Doxorubicin Delivery: Cytotoxicity and Mechanisms Involved", Molecular Therapy, 2010, pp. 101-108, vol. 18, No. 1.
Yamamon, "Transcatheter arterial chemoembolization", Journal of Japan, 2014, pp. 87-92, vol. 103.

\* cited by examiner

COMPOSITION FOR HEPATIC ARTERIAL CHEMOEMBOLIZATION USING HUMAN SERUM ALBUMIN NANOPARTICLES CARRYING ANTICANCER AGENT, AND METHOD FOR PRODUCING SAME

STATEMENT REGARDING GOVERNMENT RIGHTS

The present invention was undertaken with the support of "Development of a chemotherapeutic agent encapsulating nanoparticle-microbubble nanocomplex for ultrasound guided hepatocellular carcinoma therapy using hepatic artery embolization: No. HI15C2797 grant funded by the Korea Health Industry Development Institute.

CROSS-REFERENCE TO RELATED APPLICATIONS

This application is a 371 of PCT/KR2017/010744, filed Sep. 27, 2017, which claims the benefit of priority from Korean Patent Application No. 10-2016-0124304, filed Sep. 27, 2016 and Korean Patent Application No. 10-2017-0125169, filed Sep. 27, 2017, the contents of each of which are incorporated herein by reference in its entirety.

TECHNICAL FIELD

The present invention relates to hepatic arterial chemoembolization, and relates to a dramatic increase in an effect of hepatic arterial chemoembolization by developing human serum albumin-based nanoparticles, which is a protein of the living body, that effectively carry an anticancer agent.

BACKGROUND ART

Recently, the development of imaging technology has enabled the detection of an exact position of cancer hidden in the body to remove the cancer using various methods such as radiation irradiation, endoscopic surgery, and the like. However, although the exact location of the cancer is found, cancer spread throughout the whole organs or attached to other organs cannot be surgically removed due to various reasons. Although liver cancer, pancreatic cancer, and the like are detected, radical surgery is often impossible.

Currently, chemoembolization, which is the most commonly performed procedure for the treatment of liver tumors, is a treatment for finding the artery that supplies nutrients to liver tumors, administering an anticancer agent into the artery, and blocking blood vessels. Liver tissue is supplied with oxygen and nutrients through the portal vein that comes from the small intestine, large intestine, and the like and through the hepatic artery that directly comes from a main artery. Normal liver tissue is supplied with blood mainly from the portal vein and tumor tissue is supplied with blood mainly from the hepatic artery. Therefore, when an anticancer agent is administered to the hepatic artery that supplies nutrients to tumors and blood vessels are blocked, normal liver tissue is not adversely affected and only tumors may be selectively necrotized. This treatment is a method that is widely applied due to no limitations according to the degree of progression of cancer, and has few limitations in subjects in need of treatment, and thus most significantly contributes to improved treatment of liver cancer. In chemoembolization, first, a catheter is inserted into the femoral artery positioned in the inguinal region to approach the hepatic artery, and then a vascular contrast medium is injected to acquire information needed for treatment, such as the position and size of tumors, blood supply patterns, and the like, and when a treatment method is determined, a thin tube having a thickness of about 1 mm is inserted through the catheter to find the target artery for surgery.

However, conventional hepatic artery chemoembolization has a limitation in that an embolic material is washed out after a certain period of time, and is accompanied by side effects such as death of normal cells that results from circulation of the embolic material along the blood vessels and spread of the drug throughout the whole body.

To address these problems, the inventors of the present invention developed human serum albumin-based nanoparticles (size: about 100 nm to about 300 nm), which is a protein of the living body, that effectively carry Adriamycin, instead of Adriamycin, which is an anticancer agent currently used in hepatic artery chemoembolization, and verified that, when the human serum albumin-based nanoparticles were applied to hepatic artery chemoembolization, an effect thereof was dramatically increased, thus completing the present invention.

DISCLOSURE

Technical Problem

The present invention aims to address the problems of conventional hepatic artery chemoembolization in that an embolic material used in the chemoembolization is washed out a certain period of time after embolization and also aims to improve an anticancer treatment effect due to long-lasting efficacy through sustained drug release.

The present invention also aims to address side effects due to the above-described limitation, such as death of normal cells that results from circulation of the drug along the blood vessels and spread thereof throughout the whole body.

Specifically, the present invention provides a novel composition applied to hepatic artery chemoembolization, which includes human serum albumin-based nanoparticles (size: about 100 nm to about 300 nm), which is a protein of the living body, that effectively carry an anticancer agent, instead of an anticancer agent currently used in hepatic arterial chemoembolization, and a method of preparing the composition.

Technical Solution

According to an embodiment of the present invention, there is provided a composition for hepatic arterial chemoembolization, including: an embolic material; and human serum albumin nanoparticles carrying a water-soluble anticancer agent.

According to another embodiment of the present invention, there is provided a composition for hepatic arterial embolization, including: an embolic material; microbubbles; and human serum albumin nanoparticles that bind to surfaces of the microbubbles and carry a water-soluble anticancer agent.

Preferably, the embolic material is lipiodol.

The water-soluble anticancer agent may be one or more selected from the group consisting of mitomycin, cisplatin, Adriamycin, and gemcitabine.

A volume ratio of the embolic material to the nanoparticles may be in a range of 1:1 to 4:1.

In addition, a volume ratio of the embolic material to the nanoparticles and the microbubbles may be in a range of 1:1 to 4:1.

A concentration of the water-soluble anticancer agent may be in a range of 1 mg/mL to 20 mg/mL.

A concentration of the nanoparticles may be in a range of 10 mg/mL to 50 mg/mL.

According to another embodiment of the present invention, there is provided a method of preparing a composition for hepatic arterial embolization, including: dispersing human serum albumin nanoparticles carrying a water-soluble anticancer agent in a computed tomography and X-ray contrast medium; and mixing the dispersed nanoparticles with embolic material.

According to another embodiment of the present invention, there is provided a method of preparing a composition for hepatic arterial embolization, including: dispersing human serum albumin nanoparticles carrying a water-soluble anticancer agent in a computed tomography and X-ray contrast medium; mixing the dispersed nanoparticles with microbubbles; and mixing a mixture of the nanoparticles and the microbubbles with an embolic material.

The computed tomography and X-ray contrast medium may be one or more selected from the group consisting of iopamidol and Pamiray.

In addition, the nanoparticles may be prepared using a method including the following processes: preparing a mixture of human serum albumin and a water-soluble anticancer agent; adjusting a pH of the prepared mixture; titrating the pH-adjusted mixture with a desolvation material; adding a particle-stabilizing material to the titrated mixture; evaporating the desolvation material after the particle-stabilizing material is added; and centrifuging the mixture from which the desolvation material is evaporated.

In another embodiment, the nanoparticles may be prepared using a method including the following processes: dissolving human serum albumin in distilled water; adjusting a pH of the resulting solution; titrating the pH-adjusted material with a desolvation material; adding a particle-stabilizing material to the titrated mixture; evaporating the desolvation material; centrifuging the mixture from which the desolvation material is evaporated; and adding a water-soluble anticancer agent to the centrifuged material to allow a reaction to occur therebetween.

In another embodiment, the nanoparticles may be prepared using a method including the following processes: dissolving human serum albumin in distilled water; adjusting a pH of the resulting solution; adding 2-imino-thiazolidine to the pH-adjusted material; performing centrifugation after 2-imino-thiazolidine is added; adding a water-soluble anticancer agent thereto after the centrifugation; and titrating the resulting mixture with a desolvation material after the water-soluble anticancer agent is added.

In another embodiment, the nanoparticles may be prepared using a method including the following processes: dissolving a water-soluble anticancer agent in chloroform; adding human serum albumin to the resulting solution; vortexing after the human serum albumin is added; performing ultrasonication after the vortexing; evaporating the chloroform after the ultrasonication; and centrifuging the material from which chloroform is evaporated.

In addition, the preparation of the nanoparticles may further include forming powder-type nanoparticles by lyophilization in a vacuum state.

Advantageous Effects

According to the present invention, an effect of hepatic arterial chemoembolization is dramatically enhanced compared to previous inventions. In particular, human serum albumin nanoparticles not only can intensively infiltrate a drug into cells effectively, but also can induce a long-term treatment effect using an effect of sustained drug release from the nanoparticles.

In addition, patients with liver cancer generally cannot produce albumin, and in the present invention, human serum albumin-based nanoparticles are used, thereby inducing an effect of injecting albumin into patients with liver cancer, and thus occurring of ascites can be prevented.

BEST MODE

Figure 1:
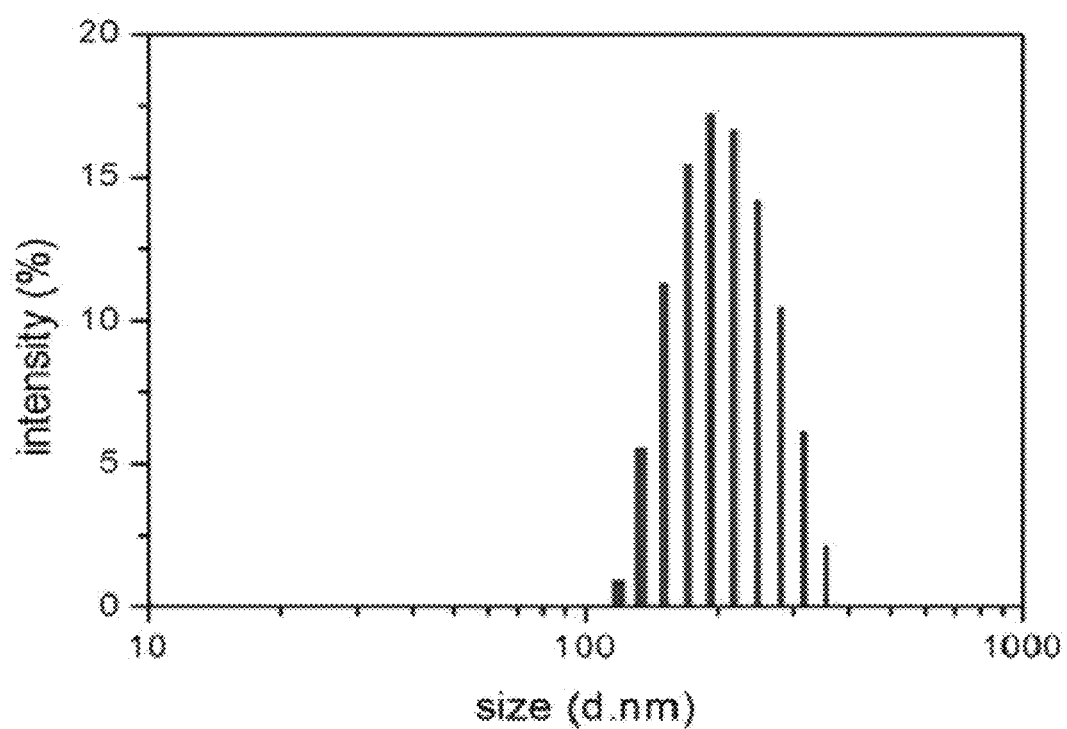
FIG. 1 is a graph showing the size distribution of human serum albumin nanoparticles 1 carrying Adriamycin.
Figure 2:
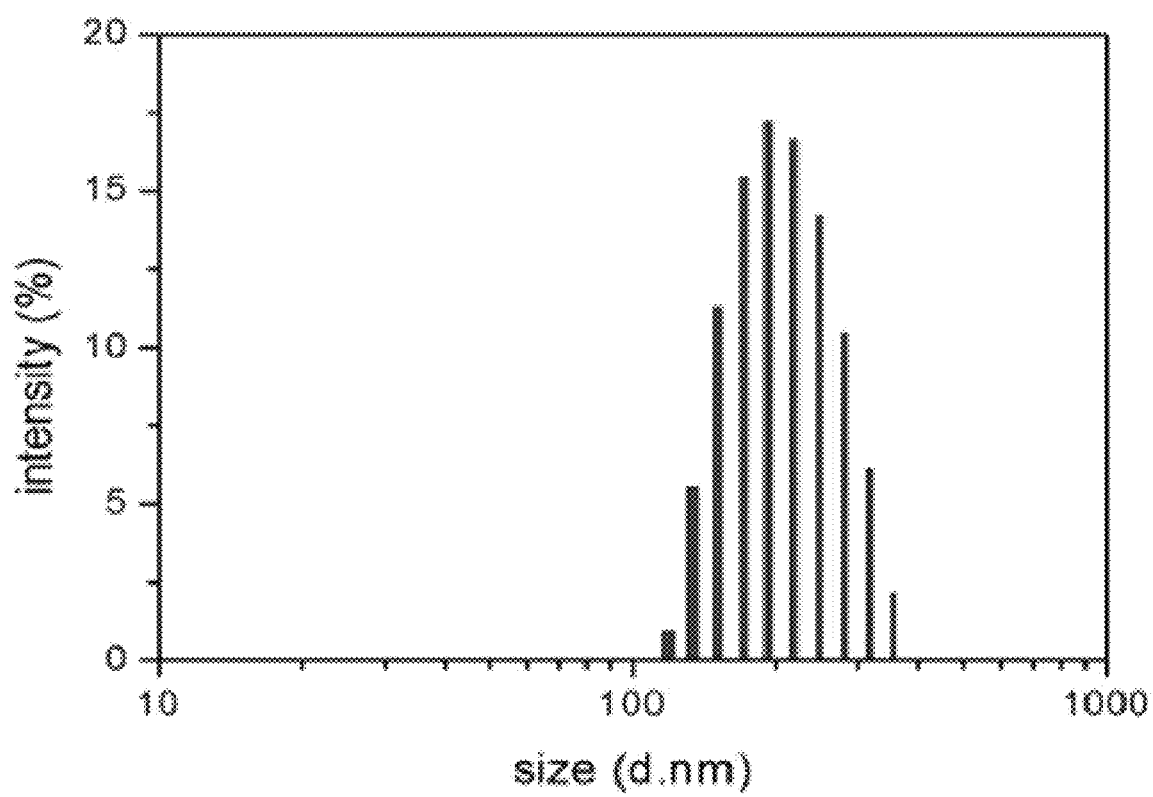
FIG. 2 is a graph showing the size distribution of human serum albumin nanoparticles 2 carrying Adriamycin.
Figure 3:
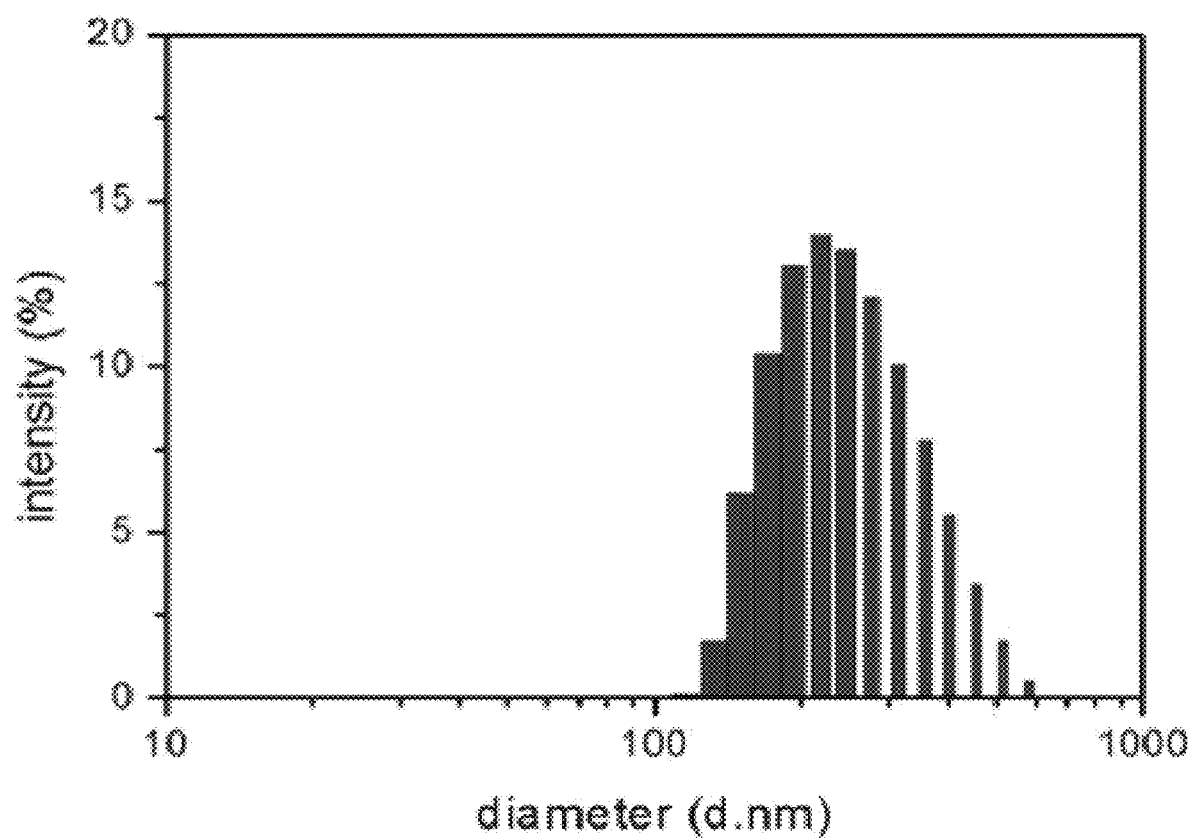
FIG. 3 is a graph showing the size distribution of human serum albumin nanoparticles 3 carrying Adriamycin.
Figure 4:
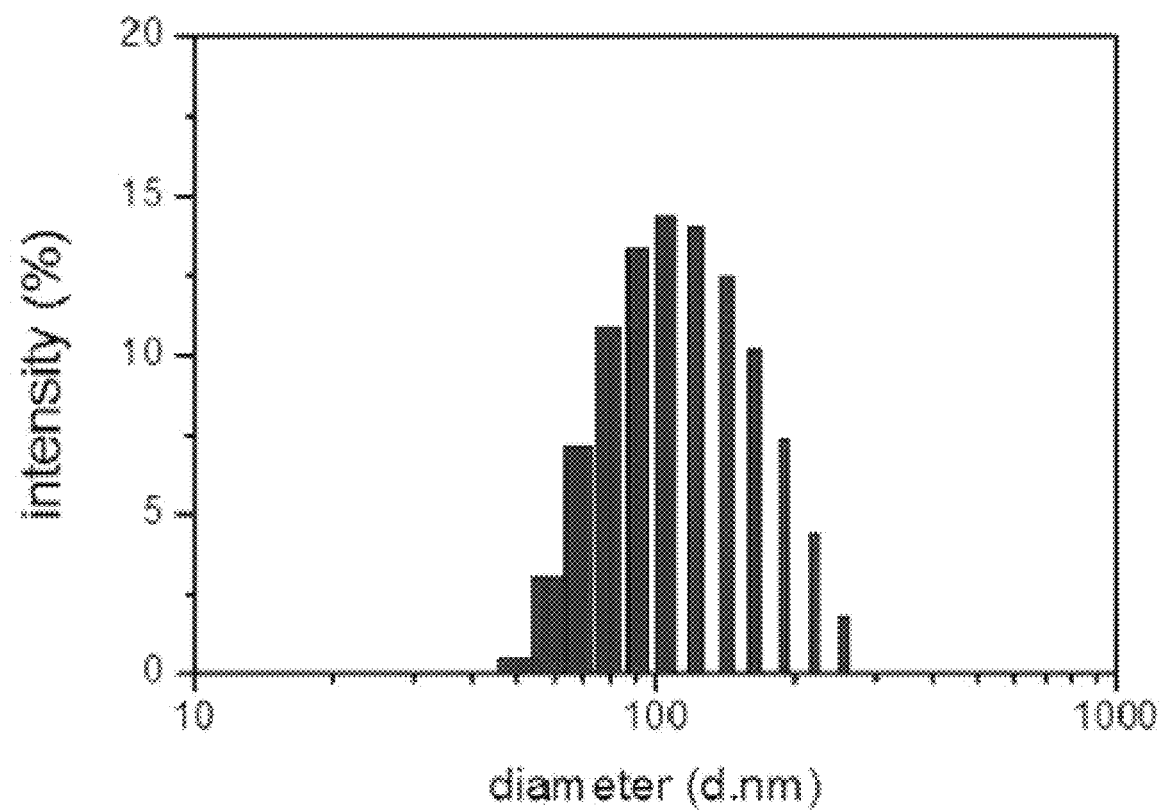
FIG. 4 is a graph showing the size distribution of human serum albumin nanoparticles carrying docetaxel.
Figure 5:
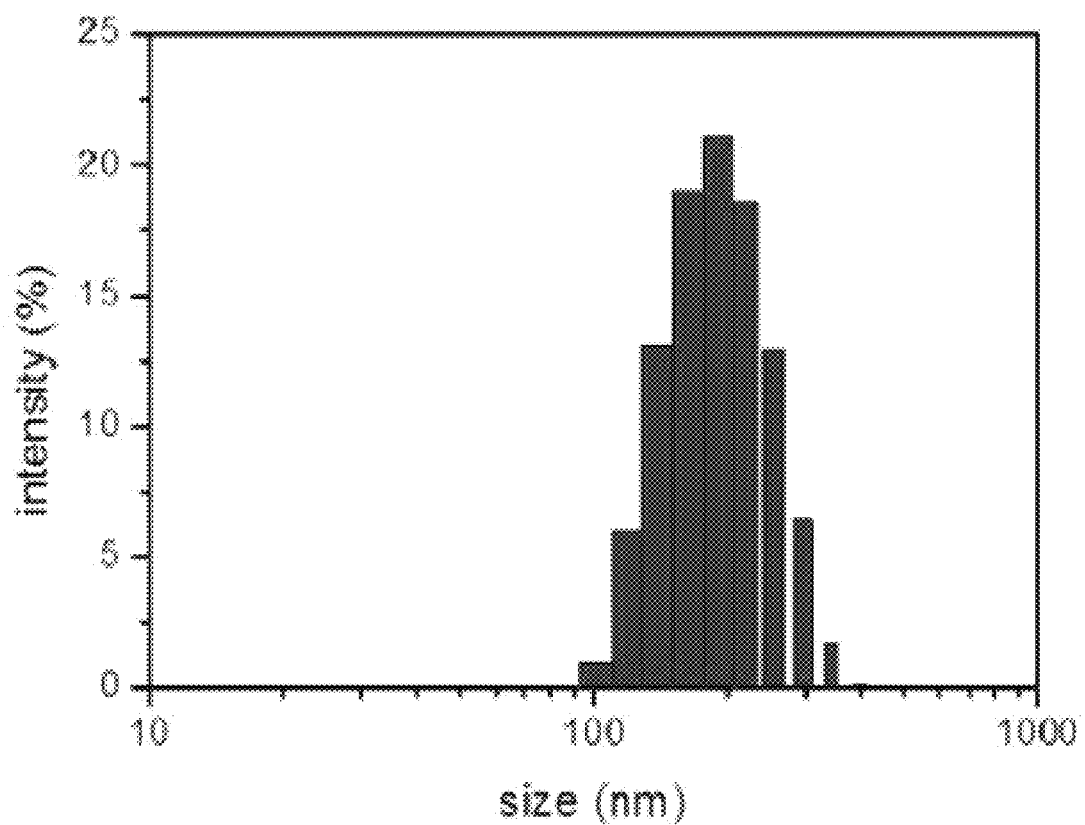
FIG. 5 is a graph showing the size distribution of human serum albumin nanoparticles carrying paclitaxel.

First, concepts needed for carrying out the present invention will be briefly described.

Distilled water is classified into primary, secondary, and tertiary distilled water according to the number of times that distilled water is purified. Distilled water used in the present invention is tertiary distilled water from which an organic material and ions are removed. Since the present invention is a biology-related invention greatly affected by organic materials, tertiary distilled water is used.

The liver is an organ that receives blood flow supply from two sources: the hepatic artery and the portal vein. Normal liver tissue is supplied with 70% to 80% of blood flow and 50% of required oxygen from the portal vein, while hepatocellular carcinoma, which is a mostly hypervascular tumor, is supplied with 90% or more of blood from the hepatic artery. Therefore, when a therapeutic material is injected through the hepatic artery, the material permeates into hepatocellular carcinoma at a high concentration compared to normal liver tissue, and even when hepatic artery blood flow is non-selectively blocked by injecting an embolic material, severe ischemia is caused only in hepatocellular carcinoma, thus enabling comparatively selective tumor treatment. This is the theoretical ground commonly applied to the treatment of hepatocellular carcinoma through the hepatic artery.

In particular, to address the above-described problems, the present invention provides a composition for hepatic arterial embolization, which includes an embolic material and human serum albumin carrying an anticancer agent.

According to the present invention, due to both an effect of sustained release of an anticancer agent loaded in human serum albumin nanoparticles carrying Adriamycin, from the particles and an effect of effectively infiltrating nano-sized particles into tumor tissues and cancer cells by transcytosis using a receptor (e.g., glycoprotein 60) overexpressed in tumor peripheral blood vessel walls and cancer cells, a synergistic effect of minimizing the exposure of normal tissue to the anticancer agent, which is a disadvantage of existing hepatic arterial chemoembolization, and inducing a long-term therapeutic effect is obtained.

As the embolic material, an oil contrast medium, especially lipiodol, may be used.

The anticancer agent may be a poorly water-soluble anticancer agent or a water-soluble anticancer agent.

The water-soluble anticancer agent may be mitomycin, cisplatin, or Adriamycin.

The water-soluble anticancer agent binds to human serum albumin through electrostatic attraction.

The poorly water-soluble anticancer agent may be docetaxel, paclitaxel, camptothecin, tamoxifen, 5-fluorouracil (5-FU), leuprolide, flutamide, vincristine, vinorelbine, valrubicin, mechlorethamine, busulfan, or the like, and binds to human serum albumin by hydrophobic-hydrophobic attraction.

A volume ratio of the embolic material to the human serum albumin nanoparticles carrying an anticancer agent is in a range of 1:1 to 4:1.

Meanwhile, to address the above-described problems, a first method of preparing human serum albumin nanoparticles carrying a water-soluble anticancer agent includes: dissolving human serum albumin and an anticancer agent in tertiary distilled water to prepare a mixture; adjusting a pH of the prepared mixture; titrating the pH-adjusted mixture with a desolvation material; adding a particle-stabilizing material to the titrated mixture; evaporating the desolvation material after the particle-stabilizing material is added; and centrifuging the mixture from which the desolvation material is evaporated.

According to another embodiment, a method of preparing human serum albumin nanoparticles carrying a water-soluble anticancer agent includes: dissolving human serum albumin in tertiary distilled water; adjusting a pH of the resulting solution; titrating the pH-adjusted material with a desolvation material; adding a particle-stabilizing material to the titrated mixture; evaporating the desolvation material after the particle-stabilizing material is added; centrifuging the mixture from which the desolvation material is evaporated; and adding an anticancer agent to the centrifuged material to allow a reaction to occur therebetween.

The anticancer agent has a concentration of 1 mg/mL to 20 mg/mL.

The human serum albumin has a concentration of 10 mg/mL to 50 mg/mL.

In the adjusting of the pH, the pH is in a range of 8 to 8.5.

The desolvation material is ethanol, and the particle-stabilizing material is an aldehyde-, amine-, carboxyl-, or thiol-based material.

The centrifugation process is performed at 10,000 rpm to 15,000 rpm for 8 minutes to 12 minutes. Preferably, the centrifugation process is repeated two to four times.

Meanwhile, to address the above-described problems, a method of preparing a composition for hepatic arterial embolization including the following steps can be provided, and a third method of preparing human serum albumin nanoparticles carrying a water-soluble anticancer agent includes: dissolving human serum albumin in tertiary distilled water; adjusting a pH of the resulting solution; adding 2-imino-thiazolidine to the pH-adjusted material; performing centrifugation after 2-imino-thiazolidine is added; adding an anticancer agent thereto after the centrifugation; and titrating the resulting mixture with a desolvation material after the anticancer agent is added.

The anticancer agent is a water-soluble anticancer agent and particularly, may be mitomycin, cisplatin, or Adriamycin, and a concentration of the anticancer agent is in a range of 1 mg/mL to 10 mg/mL.

A concentration of the human serum albumin nanoparticles is in a range of 10 mg/mL to 50 mg/mL.

In the adjusting of the pH, the pH is in a range of 8 to 8.5.

For the amount of 2-imino-thiazolidine used in the adding of the 2-imino-thiazolidine, a molar ratio of human serum albumin to 2-imino-thiazolidine is 1:10 to 30.

The centrifugation process is performed at 3,000 rpm to 5,000 rpm for 2 minutes to 4 minutes.

Meanwhile, to address the above-described problems, a method of preparing human serum albumin nanoparticles carrying a poorly water-soluble anticancer agent includes: dissolving an anticancer agent in chloroform; adding human serum albumin to the resulting solution; vortexing after the human serum albumin is added; performing ultrasonication after the vortexing; evaporating the chloroform after the ultrasonication; and centrifuging the material from which chloroform is evaporated.

The anticancer agent is a poorly water-soluble anticancer agent, and particularly, may be docetaxel, paclitaxel, camptothecin, tamoxifen, 5-fluorouracil (5-FU), leuprolide, flutamide, vincristine, vinorelbine, valrubicin, mechlorethamine, busulfan, or the like, and a concentration of the anticancer agent is in a range of 1 mg/mL to 10 mg/mL.

A concentration of the human serum albumin nanoparticles is in a range of 10 mg/mL to 50 mg/mL.

The centrifugation process is performed at 10,000 rpm to 15,000 rpm for 8 minutes to 12 minutes, and this process is repeated two to four times.

The human serum albumin nanoparticles carrying a water-soluble anticancer agent or a poorly water-soluble anticancer agent is prepared using one of the above-described four methods.

The human serum albumin nanoparticles have a size of 100 nm to 300 nm, preferably 200 nm.

In addition, to apply this to hepatic arterial chemoembolization, the solvent has to be replaced with a computed tomography and X-ray contrast medium. Therefore, to change a preparation into a powder form by lyophilizing particles, 1% to 5% of cryo-protection materials are added, and then first lyophilized at −70° C. or less, followed by lyophilization at −70° C. in a vacuum state, thereby changing the preparation into a powder form. As the cryo-protection materials used in this case, polyethylene glycol (PEG), sucrose, dextran, and the like may be used.

The computed tomography and X-ray contrast medium for re-dispersing the lyophilized human serum albumin nanoparticles carrying an anticancer agent may be iopamidol, Pamiray, or the like, and may be variously selected depending on a specific gravity thereof. For the selection of the specific gravity, a contrast medium having a specific gravity that enables uniform dispersion of lipiodol and anticancer agent-containing human serum albumin nanoparticles into an emulsion is selected, and powder-type anticancer agent-containing human serum albumin nanoparticles are dissolved therein.

The lyophilized anticancer agent-containing human serum albumin nanoparticles are re-dispersed in the above-described contrast medium, and then the resulting dispersion and lipiodol are mixed in a ratio of 1:1 to 4 (Vol:Vol), followed by 3-way pumping, thereby preparing an anticancer agent-containing human serum albumin nanoparticle/lipiodol emulsion.

According to another embodiment of the present invention, there is provided a composition for hepatic arterial embolization, which includes: an embolic material; microbubbles; and human serum albumin nanoparticles that bind to surfaces of the microbubbles and carry a water-soluble anticancer agent. As such, by binding the nanoparticles to the microbubbles, a contrast effect using microbubbles may also be obtained.

According to another embodiment of the present invention, there is provided a method of preparing a composition for hepatic arterial embolization, including: dispersing human serum albumin nanoparticles carrying a water-soluble anticancer agent in a computed tomography and X-ray contrast medium; mixing the dispersed nanoparticles with microbubbles; and mixing a mixture of the nanoparticles and the microbubbles with an embolic material.

The same contents as those described above may be applied to specific configurations of the composition for hepatic arterial embolization and the method of preparing the composition.

Hereinafter, the present invention will be described in further detail with reference to the following examples. However, it will be obvious to those of ordinary skill in the art that these examples are provided only to more particularly describe the present invention and are not intended to limit the scope of the present invention in accordance with the essence of the present invention.

MODE OF THE INVENTION

Preparation Example 1

Method 1 for Preparing Human Serum Albumin Nanoparticles Carrying Adriamycin, which is a Hydrophilic Anticancer Agent Human serum albumin nanoparticles carrying Adriamycin may be prepared using an effect of aggregation of proteins due to a polarity difference. Furthermore, Adriamycin may be more effectively carried by inducing electrostatic binding using characteristics of positively charged Adriamycin and negatively charged human serum albumin. According to an experimental method, three types of human serum albumin nanoparticles carrying Adriamycin may be produced.

1.1 Preparation Method 150 mg of human serum albumin and 5 mg of Adriamycin are dissolved in 3 mL of tertiary distilled water, and then the resulting solution is stirred for about 2 hours so that Adriamycin is effectively bound to human serum albumin. Subsequently, NaOH is added to the mixed solution of human serum albumin and Adriamycin to adjust the pH thereof to about 8.0 to about 8.5 using a pH meter. Thereafter, the resulting mixture is titrated with ethanol so that the Adriamycin-bound human serum albumin can be aggregated to nanometer size. Aggregation may be observed by a change in the turbidity of the resulting solution. After observing a change in the turbidity of the resulting solution titrated with 5 mL of ethanol, the aggregated human serum albumin to which Adriamycin is bound is cross-linked and glutaraldehyde is added thereto to induce stabilization. The glutaraldehyde is added as an 8% solution in an amount of 10 μl. The stability of the human serum albumin nanoparticles carrying Adriamycin may be controlled by the amount of glutaraldehyde added. Thereafter, stirring is carried out overnight to allow a reaction to sufficiently occur and a process of vaporizing the titrated ethanol is simultaneously performed. To obtain only human serum albumin nanoparticles carrying Adriamycin, which have been sufficiently reacted and stabilized, centrifugation is performed at 12,000 rpm for 10 minutes to remove non-granulated Adriamycin-bound human serum albumin, and this process is repeated three times to increase purity.

The size of the human serum albumin nanoparticles carrying Adriamycin may be measured using a dynamic light scattering method, and the morphology of the nanoparticle form may be observed through an electron microscope image. In addition, quantitative analysis of Adriamycin loaded in the human serum albumin nanoparticles carrying Adriamycin may be obtained by a difference between the amount of initially administered Adriamycin and the amount of unloaded Adriamycin, and the unloaded Adriamycin may be quantitatively analyzed by HPLC.

1.2 Analytical Characterization

As a result of analyzing the size of particles using a dynamic light scattering method, the particles have a size of 200.4±50.7 nm, and also have a uniform particle size distribution. In addition, Adriamycin loaded in the nanoparticles has a loading effect of about 89.64%.

Preparation Example 2

Method 2 for Preparing Human Serum Albumin Nanoparticles Carrying Adriamycin, which is a Hydrophilic Anticancer Agent 2.1 Preparation Method Human serum albumin nanoparticles 2 carrying Adriamycin are a preparation produced by slightly changing the prepared human serum albumin nanoparticles 1 carrying Adriamycin such that a disulfide bond is induced instead of using glutaraldehyde administered for stabilization. The disulfide bond can be formed by inducing a reaction between the thiol group in human serum albumin and 2-iminothiazolidine. To induce the thiol group, first, 150 mg of human serum albumin is dissolved in 3 mL of tertiary distilled water, and then a pH thereof is adjusted to 8.0 to 8.5. Subsequently, 6 mg of 2-imino-thiazolidine is added thereto to allow a reaction to occur therebetween for 1 hour so that a thiol group is introduced into the human serum albumin. After sufficient reaction, centrifugation is performed using a 3000 Da membrane at 4,000 rpm for 3 minutes to remove non-introduced 2-imino thiazolidine. 5 mg of Adriamycin is added to the unseparated thiol group-induced human serum albumin and stirred for 1 hour so that the Adriamycin is effectively bound to the thiol group-induced human serum albumin. Thereafter, the resulting mixture is titrated with about 5 mL of ethanol and stirred overnight.

Then, a process of collecting human serum albumin nanoparticles carrying Adriamycin after increasing the purity thereof and an analysis method are the same as those used for human serum albumin nanoparticles 1 carrying Adriamycin.

2.2 Analytical Characterization

As a result of analyzing the size of particles using a dynamic light scattering method, the particles have a size of 193.8±69.7 nm, and also have a uniform particle size distribution. In addition, Adriamycin loaded in the particles has a loading effect of about 70.35%.

Preparation Example 3

Method 3 for Preparing Human Serum Albumin Nanoparticles Carrying Adriamycin, which is a Hydrophilic Anticancer Agent 3.1 Preparation Method Human serum albumin nanoparticles 3 carrying Adriamycin are prepared by effectively loading Adriamycin in human serum albumin through binding therebetween by an electrostatic force. First, to prepare human serum albumin nanoparticles in which Adriamycin is not loaded, 150 mg of human serum albumin is dissolved in 3 mL of tertiary distilled water and the resulting solution is continuously stirred. After sufficient dissolving, NaOH is added thereto to adjust the pH of the resulting solution to 8.0 to 8.5. Subsequently, to aggregate the human serum albumin, the resulting solution is titrated with about 5 mL of ethanol, and then 10 µl of 8%-glutaraldehyde is added thereto to cross-link the resulting mixture, followed by stirring overnight. After sufficient cross-linking overnight, centrifugation is performed at 12,000 rpm for 10 minutes to collect only the prepared human serum albumin nanoparticles, thereby removing non-granulated human serum albumin. To load Adriamycin into the collected human serum albumin nanoparticles, 5 mg of Adriamycin is added to the human serum albumin nanoparticles to allow a reaction to occur therebetween for 1 hour.

3.2 Analytical Characterization

As a result of analyzing the size of particles using a dynamic light scattering method, the particles have a size of 246.9±79.3 nm, and also have a uniform particle size distribution. In addition, Adriamycin loaded in the particles has a loading effect of about 45.95%.

Preparation Example 4

Method of Preparing Human Serum Albumin Nanoparticles Carrying Poorly Water-Soluble Anticancer Agent (Docetaxel)

A method of preparing human serum albumin nanoparticles effectively carrying a hydrophobic anticancer agent is as follows. Docetaxel, a hydrophobic anticancer drug, is dissolved in chloroform at a concentration of 10 mg/mL to prepare a stock solution. In addition, after preparing 3 mL of a human serum albumin solution at a concentration of 50 mg/mL, 100 µl to 200 µl of a previously prepared docetaxel stock solution is added thereto, followed by vortexing at a high speed. By vortexing, a small-sized docetaxel emulsion dissolved in chloroform is prepared, and then ultrasonication is performed for 2 minutes under a condition of 1 cycle at 100% amplitude, thereby preparing an emulsion carrying an anticancer agent solution therein and consisting of a human serum albumin shell. After confirming that the prepared emulsion is coated with HSA, the chloroform is evaporated overnight in a vacuum state. At this time, it is important to rapidly evaporate the chloroform to prevent an explosion. After the chloroform is completely removed, centrifugation is performed at 12,000 rpm for 10 minutes to remove non-granulated human serum albumin and docetaxel. This process is repeated three times to obtain only docetaxel-containing human serum albumin nanoparticles that are definitely prepared.

Preparation Example 5

Method of Preparing Human Serum Albumin Nanoparticles Carrying Poorly Water-Soluble Anticancer Agent (Paclitaxel)

A method of preparing human serum albumin nanoparticles effectively carrying a hydrophobic anticancer agent is as follows. Paclitaxel, a hydrophobic anticancer drug, is dissolved in chloroform at a concentration of 10 mg/mL to prepare a stock solution. In addition, after preparing 3 mL of a human serum albumin solution at a concentration of 50 mg/mL, 100 µl to 200 µl of a previously prepared paclitaxel stock solution is added thereto, followed by vortexing at a high speed. By vortexing, a small-sized paclitaxel emulsion dissolved in chloroform is prepared, and then ultrasonication is performed for 2 minutes under a condition of 1 cycle at 100% amplitude, thereby preparing an emulsion carrying an anticancer agent solution therein and consisting of a human serum albumin shell. After confirming that the prepared emulsion is coated with HSA, the chloroform is evaporated overnight in a vacuum state. At this time, it is important to rapidly evaporate the chloroform to prevent an explosion. After the chloroform is completely removed, centrifugation is performed at 12,000 rpm for 10 minutes to remove non-granulated human serum albumin and paclitaxel. This process is repeated three times to obtain only paclitaxel-containing human serum albumin nanoparticles that are definitely prepared.

Experimental Example 1—Drug Release Behavior Experimental Analysis

To verify an effect of Adriamycin-bound human serum albumin nanoparticles exhibiting long-lasting efficacy when applied to hepatic arterial chemoembolization, by releasing the drug sufficiently for a long period of time, first, drug release behaviors of Adriamycin-bound human serum albumin nanoparticles 1, 2, and 3 are analyzed in vitro. In addition, the human serum albumin nanoparticles and lipiodol, which is an embolic material, are mixed in various ratios using the same method as that used in hepatic arterial chemoembolization to be changed into an emulsion form, and the released Adriamycin is quantitatively analyzed to measure drug release behaviors.

1.1 Experimental Method

To analyze Adriamycin released from the Adriamycin-bound human serum albumin nanoparticles, 1 mL (Adriamycin content: 5 mg) of each of the prepared samples is injected into a 2000 Da dialysis membrane and completely sealed. The resulting structure is added to a tube containing 10 mL of phosphate buffer saline and shaken at 37° C., and the dialysis membrane is transferred to a tube containing 10 mL of phosphate buffer saline at a predetermined time point to obtain each sample every time point. Groups of prepared samples are as follows:

Group 1.—free Adriamycin in phosphate buffer saline (free DOX (PBS)) or contrast media (free DOX(Pamiray))
   free Adriamycin & lipiodol with volume ratio of 1:4 (free DOX (1:4))

human serum albumin nanoparticles carrying Adriamycin in phosphate buffered saline (DOX-HSA-NPs (PBS)) or a contrast medium (DOX-HSA-NPs (Pamiray))

human serum albumin nanoparticles carrying Adriamycin & lipiodol in a volume ratio of 1:4 (DOX-HSA-NPs (1:4))

Group 2.—human serum albumin nanoparticles carrying Adriamycin & lipiodol in a volume ratio of 1:1, 1:2, 1:3, and 1:4

1.2 Experimental Results

Figure 6:
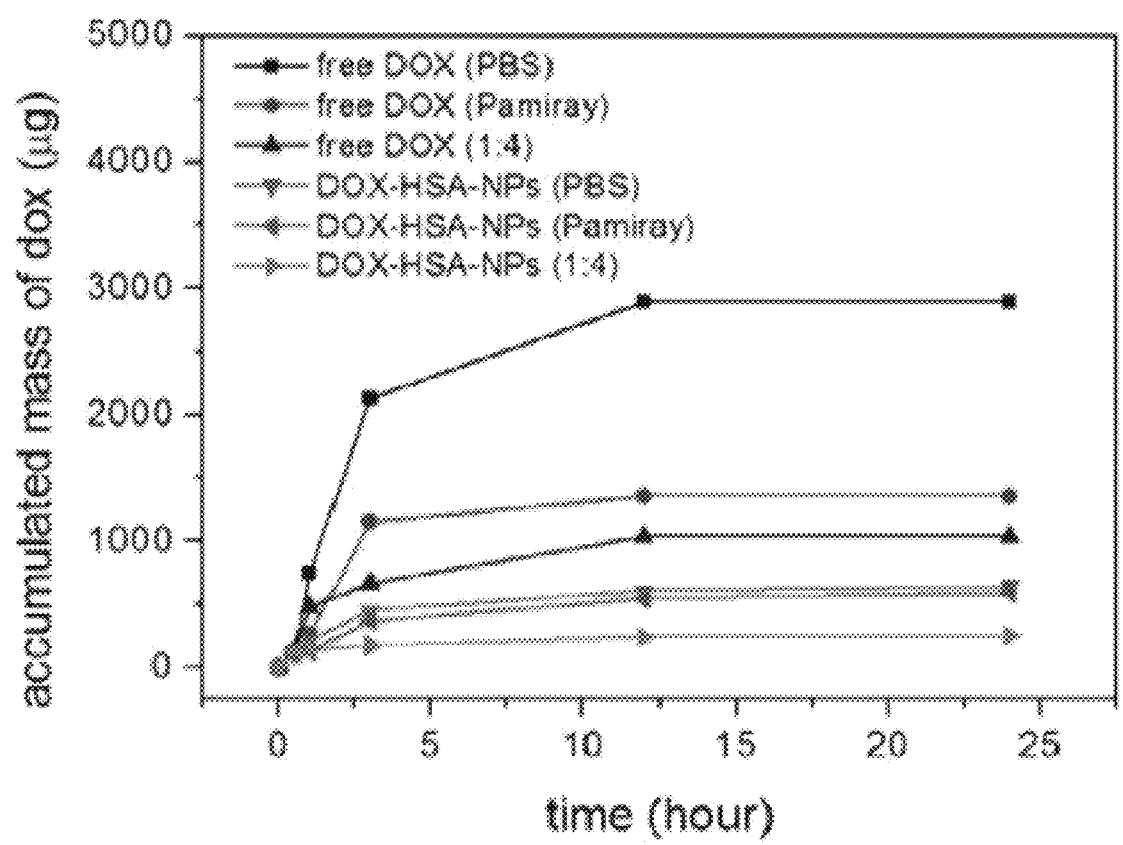
FIG. 6 is a graph showing the drug release behavior analysis of Group 1 over time.

FIG. 6 illustrates results of analyzing a drug release behavior of group 1. A free Adriamycin group (free DOX) exhibits most release of the drug within 3 hours, and a free Adriamycin group (free DOX (Pamiray)) dispersed in a contrast medium having a high specific gravity exhibits a slight delay in drug release time. In addition, a free Adriamycin group (free DOX (1:4)) in the form of an emulsion by mixing with lipiodol is in an emulsion form encapsulated in lipiodol and exhibits a sustained release effect by reducing a drug release rate, as compared to the free DOX (PBS) group and the free DOX (Pamiray) group.

Compared to the free Adriamycin groups, groups of human serum albumin nanoparticles carrying Adriamycin are basically materials capable of inducing a long-term sustained release effect due to characteristics of the human serum albumin nanoparticles and all the groups exhibit a sustained drug release effect. Unlike the free Adriamycin groups that mostly release the drug within a short period of time, in all the groups of human serum albumin nanoparticles carrying Adriamycin, the amount of an initially released drug is very insignificant, i.e., within 1 mg, from which it is determined that these groups are preparations expected to provide a long-term treatment effect by sustained release of the drug. In particular, the human serum albumin nanoparticles carrying Adriamycin in the form of an emulsion by mixing with lipiodol in a ratio of 1:4 barely exhibit a drug release effect at the initial stage and may be expected to provide long-term efficacy due to the greatest sustained release effect.

Figure 7:
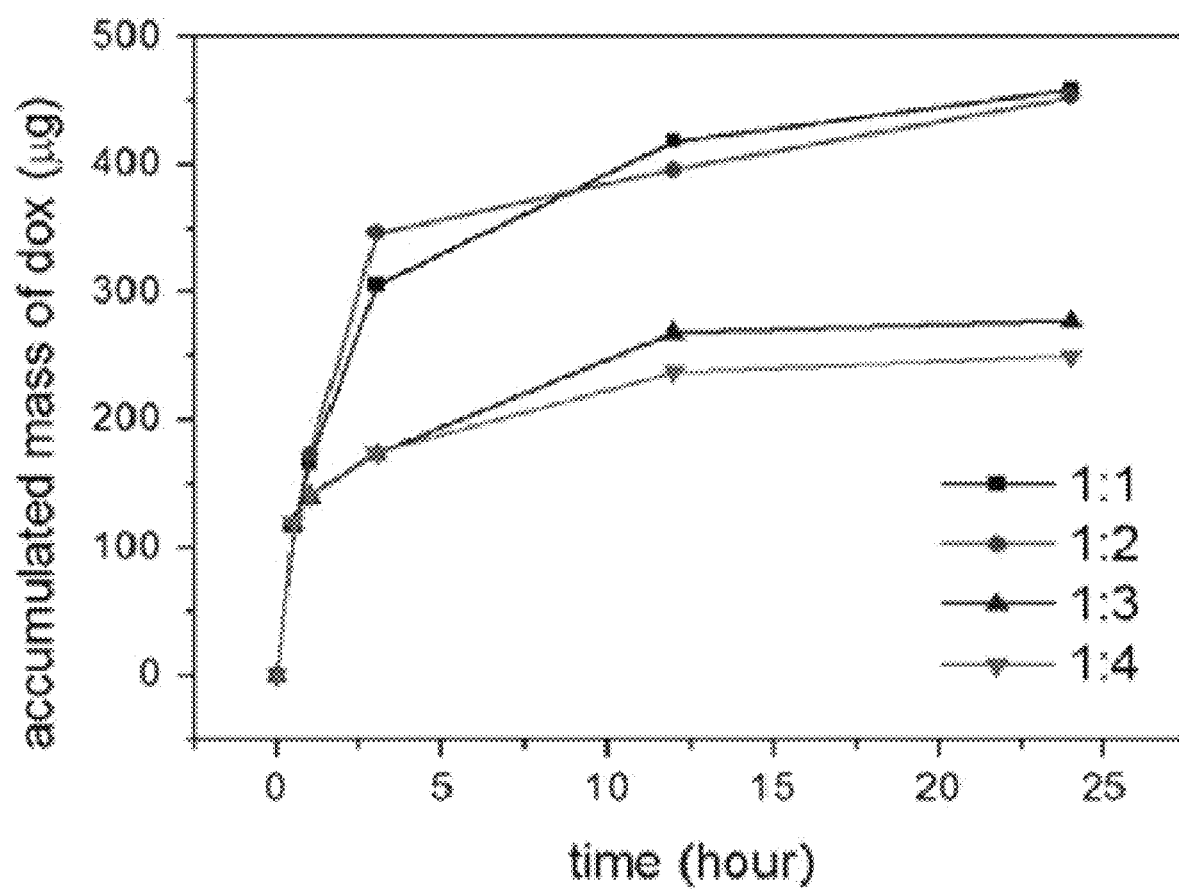
FIG. 7 is a graph showing the drug release behavior analysis of Group 2 over time.
Figure 8:
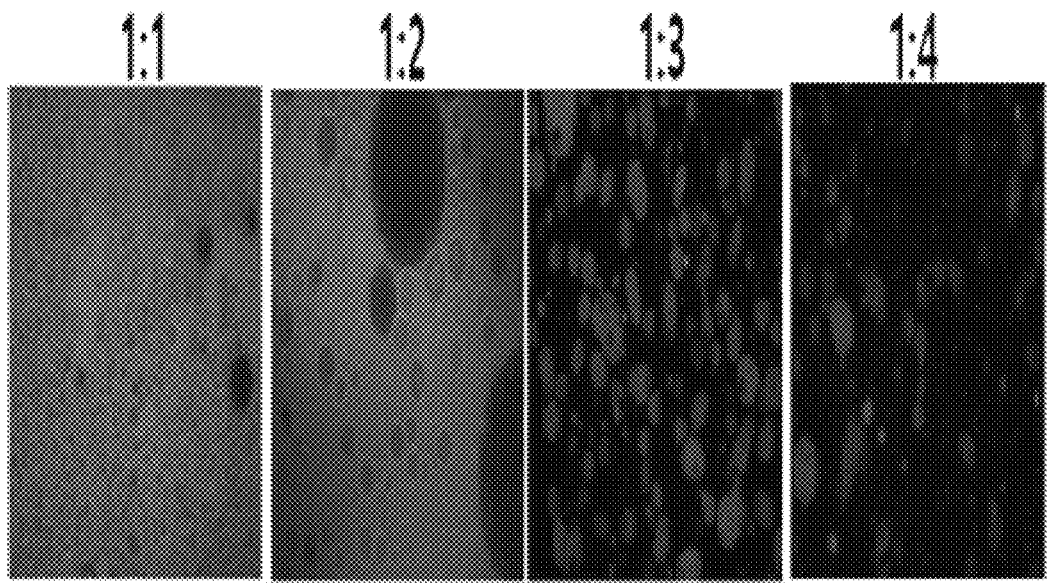
FIG. 8 is a fluorescence image (Red: Adriamycin) of Group 2.

For application to hepatic arterial chemoembolization, to obtain an optimum mixing ratio of the nanoparticles to lipiodol, as a result of adjusting the mixing ratio of the nanoparticles to lipiodol to 1:1, 1:2, 1:3, and 1:4, as illustrated in FIG. 7, the optimum mixing ratio is obtained as 1:3 and 1:4. Emulsions in the ratios of 1:1 and 1:2 exhibit more release of the drug within a short period of time compared to emulsions in the ratios of 1:3 and 1:4. In addition, as illustrated in FIG. 8, the emulsions in the ratios of 1:1 and 1:2 are in the form of emulsions in which lipiodol is covered by the human serum albumin nanoparticles carrying Adriamycin, instead of an emulsion in which the human serum albumin nanoparticles carrying Adriamycin are covered by lipiodol, and thus are preparations in which an embolization effect cannot be significantly expected. Therefore, the emulsion in the ratio of 1:4 is determined as a preparation capable of maximizing an embolization effect and a sustained drug release effect.

Experimental Example 2—Analysis of Anticancer Effect by Hepatic Arterial Chemoembolization Using Disease Animal Model Anticancer effects of an emulsion prepared by mixing the developed human serum albumin nanoparticles carrying Adriamycin and lipiodol in a ratio of 1:4 and an emulsion prepared by mixing Adriamycin and lipiodol in a ratio of 1:4, which is a method currently used in hepatic arterial chemoembolization are verified through an animal experiment. The animal model is a VX2 carcinoma rabbit model, and a liver cancer animal model is produced by directly transplanting cancer cells into the liver and growing the cancer cells and evaluated.

2.1 Experimental Method

By using a VX2 carcinoma rabbit model, a catheter is placed into the artery of rabbits while observing X-ray images, and then 200 µl of each of the free Adriamycin & lipiodol emulsion (ratio of 1:4) and the human serum albumin nanoparticles carrying Adriamycin & lipiodol emulsion (ratio of 1:4) is added thereto to perform hepatic arterial chemoembolization. At this time, the amount of Adriamycin added in each case is the same as 1 mg, and lipiodol is also injected at the same dose, so that an anticancer effect by embolization is controlled equally. 3 days and 7 days after each sample is injected, tumors are collected to analyze an anticancer effect. Experimental groups are as follows:

Group-Adriamycin-loaded human serum albumin nanoparticles & lipiodol emulsion (ratio of 1:4), collected after 3 days (001)

Adriamycin-loaded human serum albumin nanoparticles & lipiodol emulsion (ratio of 1:4), collected after 7 days (002)

free Adriamycin & lipiodol emulsion (ratio of 1:4), collected after 3 days (003)

free Adriamycin & lipiodol emulsion (ratio of 1:4), collected after 7 days (004)

2.2 Experimental Results

Figure 9:
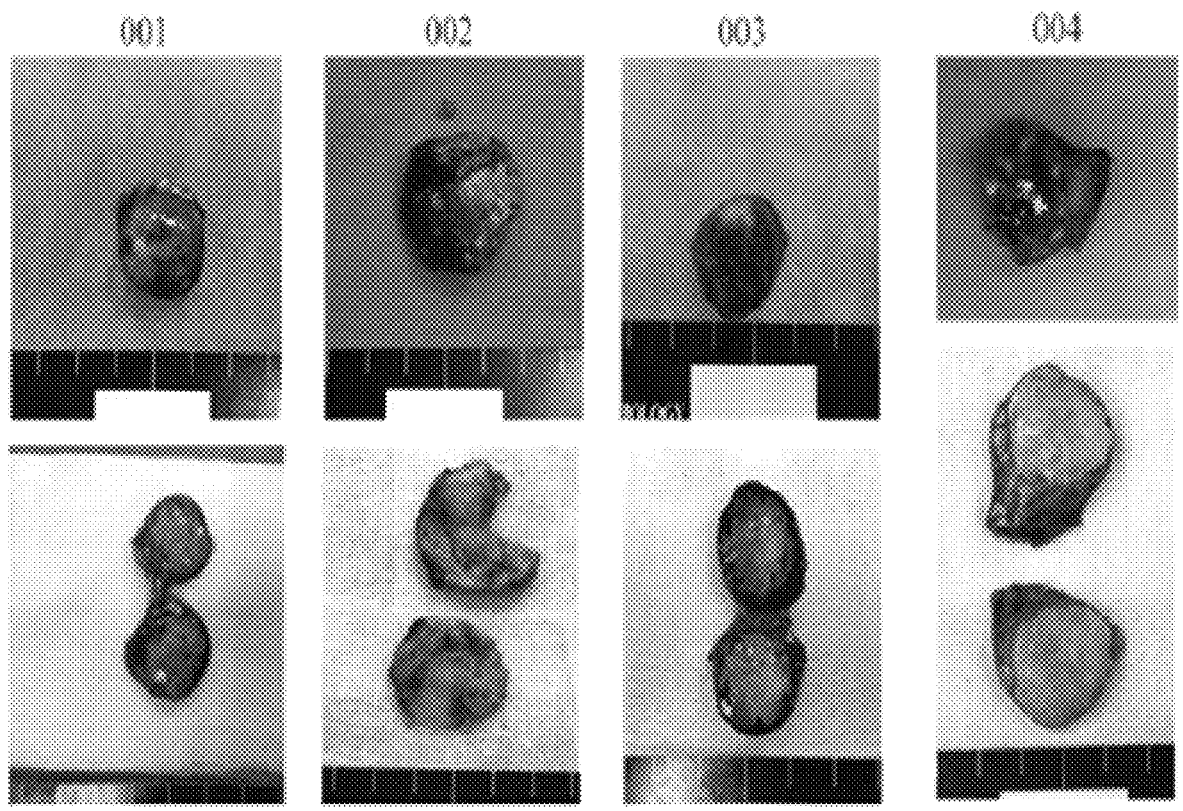
FIG. 9 is a set of images showing comparative analysis results of anticancer effects 3 days and 7 days after hepatic arterial chemoembolization.

FIG. 9 shows anticancer effects after 3 days and 7 days. When free Adriamycin and Adriamycin-loaded human serum albumin were applied to embolization, both groups exhibited an effect of effectively killing liver cancer cells. However, in the case of treatment with free Adriamycin, surviving cancer cells were observed in the peripheral region on the basis of the results (004) after 7 days, whereas both groups (001 and 002) treated with the Adriamycin-loaded human serum albumin exhibited a result of effectively killing liver cancer cells, which indicates a maximized effect by hepatic arterial chemoembolization. Furthermore, a sustained drug release effect is anticipated, and thus a long-term anticancer effect is expected.

Experimental Example 3

Data Analysis of Results of Performing Cell Viability Assay in In Vitro Release-Completed State The above experiment is the result of performing a cell viability assay using Adriamycin-carrying human serum albumin nanoparticles in an in vitro release-completed state. As can be seen from the left image of FIG. 10, the Adriamycin-carrying human serum albumin nanoparticles at the time when release no longer proceeds show a red color and still carry Adriamycin.

Figure 10:
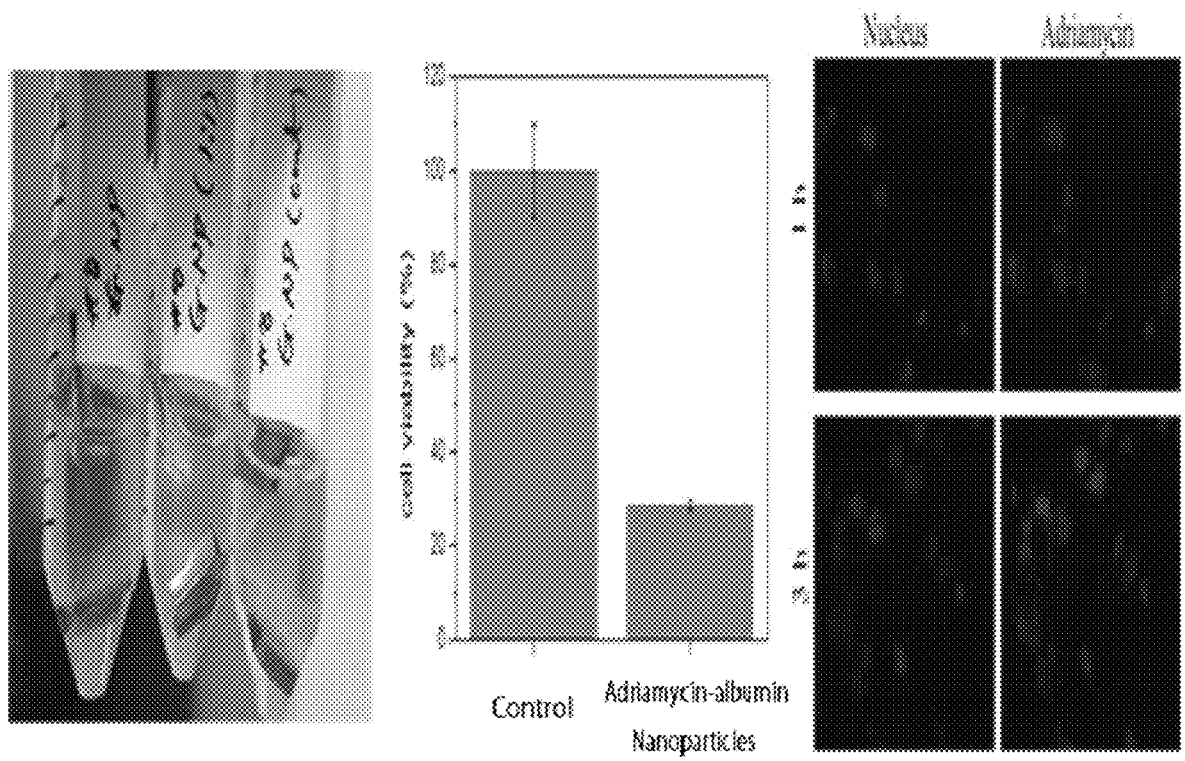
FIG. 10 is a set of images showing results of performing a cell viability assay using human serum albumin nanoparticles carrying Adriamycin in a state in which in vitro release has been completed.

Quantitative analysis results of an anticancer effect using the particles are illustrated in a graph in the middle of FIG. 10, and particles present in the state of still carrying Adriamycin are degraded when they infiltrate into cells and thus still have an anticancer effect, thereby inducing the death of cancer cells.

Based on the fluorescence image on the right side of FIG. 10, it was verified that Adriamycin was detected in the nuclei of cells. That is, it can be seen that Adriamycin-human serum albumin nanoparticles are degraded in cells to release the loaded Adriamycin, and the released Adriamycin infiltrates into the nuclei of cells, thereby inducing an anticancer effect.

Thus, it can be seen that Adriamycin released from Adriamycin-carrying human serum albumin nanoparticles exhibits an anticancer effect, and the albumin particles are degraded when infiltrating into cells, and thus Adriamycin is secondarily released, thus exhibiting an anticancer effect.

Preparation Example 6—Preparation of Microbubbles 1,2-distearoyl-sn-glycero-3-phosphocholine (DSPC) and 1,2-dioleoyl-sn-glycero-3-phosphoethanolamine-n[poly(ethyleneglycol)]$_{2000}$-N-hydroxysuccinimide (DSPE-PEG$_{2000}$-NHS), as lipids are dissolved in chloroform in a molar ratio of 9:1, and then the chloroform is completely evaporated using a rotary evaporator to form a thin lipid film.

Subsequently, 0.01 M phosphate buffered saline (PBS, pH 7.4) is added to the thin lipid film and the lipids are dissolved while the temperature is maintained at 55° C. to 60° C. Thereafter, a container containing the mixed solution is filled with C3F8 gas, and then subjected to mechanical agitation for 45 seconds to form microbubbles.

Preparation Example 7—Formation of alb-MB-TACE 7.1 Preparation Method

1. A doxorubicin.HCl-loaded human serum albumin nanoparticle (DOX-HSA NPs) pellet is dispersed in Pamiray, which is a contrast medium, to a certain concentration (e.g., 6.25 mg/ml). Vortexing is used to sufficiently disperse the nanoparticles.

2. Microbubbles (0.5 mg/ml or 1 mg/ml) are produced and placed in a 5 ml syringe, 1 ml of PBS is further added to a glass vial containing the microbubbles to recover the microbubbles, and then the microbubbles are placed in a 5 ml syringe.

3. The 5 ml syringe containing the microbubbles was placed in a centrifuge and centrifuged at 225×g for 10 minutes so that the microbubbles are collected at an upper layer portion. Thereafter, the microbubbles at the uppermost layer portion are left and the solution inside the syringe is discarded.

4. DOX-HSA NPs and the microbubbles are mixed in sufficient amounts and pipetted to cause a sufficient reaction to occur. Subsequently, a reaction is allowed to occur at room temperature for 1 hour.

5. For the preparation of an alb-MB-TACE preparation, a certain amount of DOX-HSA NPs-MB dissolved in Pamiray is placed in an e-tube or a glass vial, and lipiodol is placed in the same 1.5 ml plastic tube or glass vial in accordance with the mixing ratio, followed by vortexing. While visually confirming sufficient mixing without layer separation, vortexing is performed for 15 seconds to 20 seconds (e.g., DOX-HSA NPs-MBs in Pamiray: lipiodol=1:2, v/v).

7.2 Analytical Characterization

Figure 11:
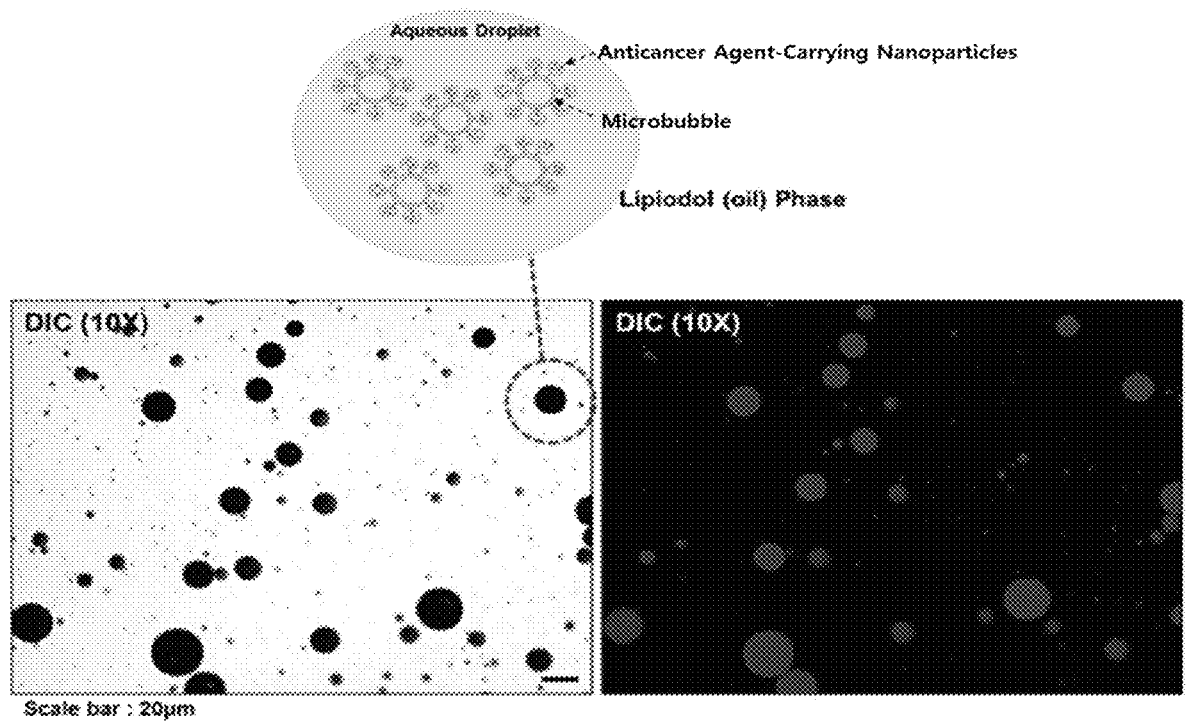
FIG. 11 is a set of DIC images of a preparation according to an embodiment of the present invention.

DIC images and a view of the alb-MB-TACE preparation are illustrated in FIG. 11. In addition, as a result of acquiring DIC images a total of five times or more, and then obtaining an average size of the preparation using a scale bar for each magnification on a microscope program, the preparation had an average diameter of 17.69±6.83

Experimental Example 4—Analysis of Anticancer Effect by Hepatic Arterial Chemoembolization Using Disease Animal Model An anticancer effect of the prepared alb-MB-TACE emulsion was verified through an animal experiment. The animal model is a VX2 carcinoma rabbit model, and a liver cancer animal model is produced by directly transplanting cancer cells into the liver and growing the cancer cells and evaluated.

4.1 Experimental Method

The alb-MB-TACE emulsion was prepared for the administration of 0.5 mg of DOX per rabbit. The preparation was injected into rabbits, and then the rabbits were irradiated with ultrasonic waves using an adult convex probe (center frequency: 1.8 MHz) for 15 minutes.

4.2 Experimental Results

Figure 12:
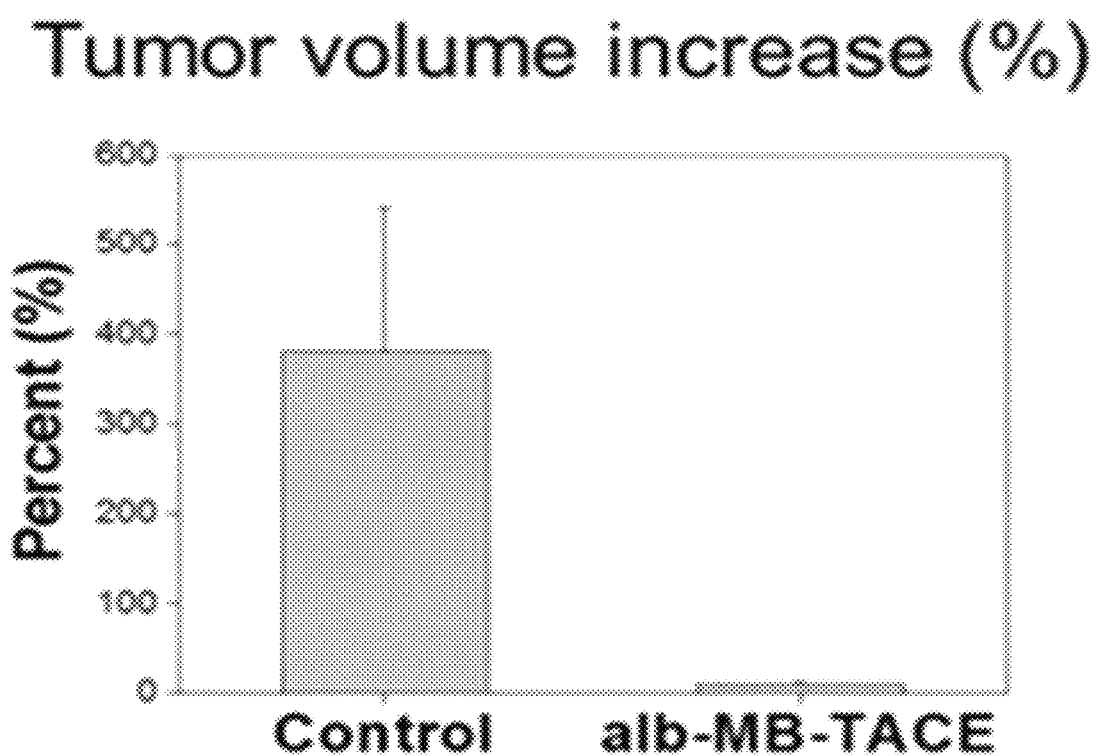
FIG. 12 illustrates liver cancer therapeutic efficacy data of a preparation according to an embodiment of the present invention.

As an evaluation of the therapeutic efficacy of alb-MB-TACE on the animal model, tumor volume change (volume inhibition ratio) results are illustrated in FIG. 12. As illustrated in FIG. 12, it can be seen that a tumor volume in a control treated with nothing is increased by about 380%, as compared to the initial tumor volume. In contrast, it can be confirmed that the tumor volume of alb-MB-TACE relative to the initial tumor volume is barely increased, i.e., by less than about 20%.

The invention claimed is:

1. A method for hepatic arterial embolization comprising:
   administering a composition comprising an effective amount of an embolic material; and an effective amount of human serum albumin nanoparticles carrying a water-soluble anticancer agent, to a subject having a liver tumor,
   wherein the water-soluble anticancer agent is loaded in the human serum albumin nanoparticles,
   wherein the composition is in the form of an emulsion in which the human serum albumin nanoparticles carrying a water-soluble anticancer agent are mixed with the embolic material,
   wherein a volume ratio of the embolic material to the human serum albumin nanoparticles is 3:1 to 4:1,
   wherein the human serum albumin nanoparticles have a size of 100 nm to 300 nm, and
   wherein the embolic material is an ethiodized oil.

2. The method of claim 1, wherein the composition further comprises:
   microbubbles; and
   wherein, the human serum albumin nanoparticles are bound to surfaces of the microbubbles, and the microbubbles are mixed with the embolic material.

3. The method of claim 1, wherein the water-soluble anticancer agent is selected from the group consisting of mitomycin, cisplatin, Adriamycin, gemcitabine, and a mixture thereof.

4. The method of claim 1, wherein a concentration of the water-soluble anticancer agent is 1 mg/mL to 20 mg/m L.

5. The method of claim 1, wherein a concentration of the nanoparticles is from 10 mg/mL to 50 mg/m L.

6. The method of claim 1, wherein the composition is prepared by a method comprising: dispersing human serum albumin nanoparticles carrying a water-soluble anticancer agent in a computed tomography and X-ray contrast medium; and
   mixing the dispersed nanoparticles with an ethiodized oil, and emulsifying the human serum albumin nanoparticles with the ethiodized oil, wherein a volume ratio of the ethiodized oil to the human serum albumin nanoparticles is 3:1 to 4:1.

7. The method of claim 6, wherein the dispersed nanoparticles are mixed with microbubbles; and the mixture of the nanoparticles and the microbubbles are mixed with the embolic material.

8. The method of claim 6, wherein the computed tomography and X-ray contrast medium comprises iopamidol.

9. The method of claim 6, wherein the water-soluble anticancer agent is selected from the group consisting of mitomycin, cisplatin, Adriamycin, gemcitabine and a mixture thereof.

10. The method of claim 6, wherein the human serum albumin nanoparticles are prepared by using a method comprising:
preparing a mixture of human serum albumin and a water-soluble anticancer agent;
adjusting a pH of the prepared mixture;
titrating the pH-adjusted mixture with a desolvation material;
adding a particle-stabilizing material to the titrated mixture;
evaporating the desolvation material after the particle-stabilizing material is added; and
centrifuging the mixture from which the desolvation material is evaporated.

11. The method of claim 6, wherein the nanoparticles are prepared using a method comprising:
dissolving human serum albumin in distilled water;
adjusting a pH of the resulting solution;
titrating the pH-adjusted material with a desolvation material;
adding a particle-stabilizing material to the titrated mixture;
evaporating the desolvation material;
centrifuging the mixture from which the desolvation material is evaporated; and
adding a water-soluble anticancer agent to the centrifuged material to allow a reaction to occur therebetween.

12. The method of claim 6, wherein the nanoparticles are prepared using a method comprising:
dissolving human serum albumin in distilled water;
adjusting a pH of the resulting solution;
adding 2-imino-thiazolidine to the pH-adjusted material;
performing centrifugation after 2-imino-thiazolidine is added;
adding a water-soluble anticancer agent thereto after the centrifugation; and
titrating the resulting mixture with a desolvation material after the water-soluble anticancer agent is added.

13. The method of claim 6, wherein the nanoparticles are powder-type nanoparticles prepared by lyophilization.

* * * * *